United States Patent
Lerman (10) Patent No.: US 6,368,295 B1
(45) Date of Patent: Apr. 9, 2002

(54) NON-INVASIVE HALO-TYPE CERVICAL BRACE

(76) Inventor: Max Lerman, 1950 Carla Ridge, Beverly Hills, CA (US) 90210

(*) Notice: Subject to any disclaimer, the term of this patent is extended or adjusted under 35 U.S.C. 154(b) by 0 days.

(21) Appl. No.: 09/413,300

(22) Filed: Oct. 6, 1999

(51) Int. Cl.$^7$ ............................... A61F 5/00; A61F 5/37
(52) U.S. Cl. ..................... 602/17; 602/18; 128/DIG. 23
(58) Field of Search ............................ 602/5, 6, 17–19, 602/32, 36, 38; 128/874, DIG. 19, 23, 845–846; 2/468

(56) References Cited

U.S. PATENT DOCUMENTS

| | | | |
|---|---|---|---|
| 2,820,455 A | * 1/1958 | Hall | 128/87 |
| 2,855,202 A | * 1/1958 | Kinne | 482/10 |
| 3,957,040 A | 5/1976 | Calabrese | 128/75 |
| 4,541,421 A | 9/1985 | Iversen et al. | 128/87 B |
| 4,620,530 A | 11/1986 | Lanier et al. | 128/75 |
| 4,953,569 A | * 9/1990 | Lonardo | 128/892 |
| 5,054,475 A | * 10/1991 | Calabrese et al. | 128/75 |
| 5,133,341 A | * 7/1992 | Singer et al. | 602/16 |
| 5,261,873 A | * 11/1993 | Bremer et al. | 602/36 |
| 5,575,763 A | * 11/1996 | Nagata et al. | 602/18 |
| 5,891,076 A | * 4/1999 | Fabo | 602/52 |

* cited by examiner

*Primary Examiner*—Denise Pothier
(74) *Attorney, Agent, or Firm*—Christie, Parker & Hale, LLP (57) ABSTRACT

A non-invasive halo-type cervical brace includes an anterior vest overlying the patient's chest and secured tightly by straps extending behind the patient's back. The vest carries a rigid frame structure, including a U-shaped halo frame extending under the patient's chin and around the sides of the patient's head. The halo frame fastens to the frame by upright supports with adjustments aligning the orientation of the halo frame around the patient's head and relative to the anterior vest. A non-invasive halo mask affixed to the halo frame includes a two-part flexible halo immobilized in a position encircling the patient's head, extending generally horizontally around the forehead, the sides and back (occipital region) of the head. The halo includes (1) a semi-rigid forehead band adjustable in length and affixed to the halo frame and extending around the forehead, and (2) a padded occipital support secured against the rear of the patient's head with pressure applied by adjustable straps extending from the occipital support to the halo frame. A flexible trapeze-type chin support affixed to the inside of the halo frame extends under the patient's chin. The chin support is adjustable to apply immobilizing pressure under the chin. The insides of the forehead band and chin support include skin adhesion layers of a non-skid material for frictional contact with the skin to enhance immobilization by avoiding relative motion between the skin and pressure applied by the halo and chin support during use.

21 Claims, 6 Drawing Sheets

NON-INVASIVE HALO-TYPE CERVICAL BRACE

FIELD OF THE INVENTION

This invention relates to cervical braces for immobilizing a patient's head, neck, and torso to avoid cervical extension, flexion, or rotation, thereby avoiding damage to the spinal cord. The invention comprises a halo mask and a skin adhesion system in combination with a fixed frame and vest apparatus which substantially immobilize the patient's head, neck, and torso, while avoiding use of invasive immobilization techniques.

BACKGROUND

Annually, approximately 10,000 people become paraplegic or quadriplegic because of spinal cord injuries, often as a result of damage to the surrounding vertebral column from fracture, dislocation, or both. Of the nearly ten million people in the U.S. who sustain head injuries annually, many also have an associated instability of the spinal column. With preexisting conditions such as spondylosis, a congenitally narrowed spinal canal, or instability of apophyseal joints of adjacent vertebrae caused by diseases such as rheumatoid arthritis, a patient may suffer severe spinal cord damage after sustaining only minor injuries.

Because hyperextension or flexion is the main cause of injury to the cervical cord, the care of patients who have undergone neck or head injuries, or who are particularly susceptible to spinal cord damage, requires immobilizing areas of the patient's body which impact the cervical region. Such immobilization prevents initial or continued spinal cord damage. Thus, during the healing process, a patient's head, neck, and torso should be properly positioned relative to each other and then immobilized to avoid cervical extension, flexion, or rotation which could result in continued or initial damage to the spinal cord.

Conventionally, a patient's head, neck, and torso are positioned in a predetermined relative orientation and then immobilized by use of a cervical brace. As shown in U.S. Pat. No. 4,620,530 to Lanier et al. and U.S. Pat. No. 4,541,421 to Iversen et al., for example, a conventional cervical brace includes a metal or non-metal ring encircling the parietal and frontal bone of a patient's skull. The ring, often referred to as a "halo," includes spaced apart skull pins which connect to the parietal bone, temporal bone, sphenoid bone, or frontal bone, or a combination of them, at various locations around the halo. The skull pins may physically penetrate the bone structure of the patient's skull, or alternatively, they may be pointed screws contacting the patient's skin surface.

U.S. Pat. No. 3,957,040 to Calabrese discloses a halo type cervical brace in which the halo portion covering the posterior part, of the patient's head is curved downward to embrace the occipital bone, as opposed to the parietal bone.

The conventional halo-type cervical brace includes a vest and frame structure affixed to the patient's upper torso. The halo is supported by the frame structure. By properly positioning the vest, halo, and skull pins relative to each other, the patient's torso, neck, and head are immobilized in a position which avoids placing stress on the spinal cord at a level which would initiate or exacerbate injury. If the patient attempts to move in a manner opposed by the fixed orientation of the halo and vest, the patient is restrained and experiences pain due to the adverse pressure applied by the skull pins directly to the patient's head. Adverse cervical extension, flexion, and/or rotation are thereby avoided.

Use of penetrating skull pins to achieve full head, neck, and torso immobilization in conventional cervical halo braces causes unnecessary discomfort for the patient and exposes the patient to possible infections at the point of pin contact. In contrast, an objective of this invention is to achieve substantially full immobilization of the patient's head, neck, and torso without use of such invasive immobilization devices.

Additionally, invasiveness of such conventional cervical braces requires the halo-vest apparatus to be fitted, maintained, and adjusted by highly skilled medical personnel. Another objective of this invention is to provide a cervical brace which can maintain a useful level of immobilization of a patient's head, neck, and torso, without requiring the same degree of medical assistance required of invasive techniques.

A further objective of this invention is to provide a non-invasive immobilization of a patient's head, neck, and torso region in a predetermined orientation without incurring any significant slippage so that substantially full immobilization of the patient's neck, head and torso can be achieved at a level that avoids adverse extension, flexion or rotation of the cervical region.

SUMMARY OF THE INVENTION

The present invention provides a non-invasive halo-type cervical brace which represents a marked improvement over existing methods and devices for achieving substantially full immobilization of a patient's neck, head, and torso to avoid adverse extension, flexion, or rotation of a patient's cervical region.

One embodiment of the invention comprises a non-invasive halo-type cervical brace which includes a reinforced anterior vest which overlies the chest region of the patient and supports an upright rigid frame structure which holds an immobilizing halo mask around the head of the patient. The rigid frame structure includes a U-shaped halo frame which extends under the chin and along the sides of the patient's head. The rigid frame structure also includes one or more vertical frame members affixed to the bottom of the halo frame and to the front of the vest by adjustable clamps which position the halo frame around the patient's head in a desired orientation. The halo mask includes a flexible generally U-shaped trapeze type sling carried within the U-shaped halo frame. The sling extends under the chin and around the sides of the patient's head generally in alignment with the U-shaped halo frame. The free ends of the sling comprise flexible straps which extend through respective slots on the halo frame and then through respective clamp buckles adjacent the halo frame. The free ends of the sling are pulled through the slots and used to adjust the length of the sling for making a snug fit under the patient's chin and around the sides of the patient's head, with the pressure being held tight by fastening the clamp buckles at the sides of the halo frame.

The U-shaped halo frame also carries a two part halo-type support which includes (1) a generally U-shaped semi-rigid forehead band which extends around the forehead and along the sides of the patient's head, and (2) a padded occipital support attached to the halo frame by flexible straps adjustable in length for securing the occipital support behind the patient's head. The U-shaped forehead band is adjustable in length and preferably comprises a pair of opposed curved bars affixed at their ends to the halo frame with their free ends overlying one another adjacent the forehead of the patient. The forehead bars are releasably secured to each other by cooperating friction fasteners for adjusting the length of the U-shaped forehead band and holding it in a fixed position along the forehead and around the sides of the patient's head. The occipital support is adjusted tightly against the back of the patient's head by its cooperating adjustable straps to apply pressure in combination with the forehead band in a manner similar to a halo encircling the patient's head.

Elongated skin adhesion layers are affixed to the inside of the U-shaped forehead band, for applying pressure to the forehead, and to the inside of the sling which extends under and applies pressure to the patient's chin. The skin adhesion layers comprise a material which provides a level of non-skid frictional contact with the skin sufficient to prevent slippage between the patient's skin and the tightly adjusted halo and chin support. Preferably, the skin adhesion layer for the inside of the forehead band is carried on a separate flexible strap having a friction fastener surface material cooperating with friction fasteners on the inside of the forehead band for releasably positioning the skin adhesion layer to the inside of the forehead band. In a preferred form of the invention, the skin adhesion layer comprises a reinforced silicone gel material capable of frictionally adhering to the patient's skin for long periods of time without detrimental effects to the patient's skin or comfort during use.

By employing the strategically positioned skin adhesion layers in combination with the halo mask, the present invention substantially immobilizes the patient's head, neck, and torso, thereby preventing the patient from adversely extending, flexing, or rotating the cervical region. Because the present invention provides substantially full immobilization of the patient's head, neck, and torso without use of invasive immobilization techniques, employing this novel cervical brace does not require the same use of highly skilled medical personnel as a conventional halo type brace with skull penetration pins. In addition, it does not expose the patient to the unnecessary discomfort of skull pin penetration into the patient's body. By eliminating the use of skull pins, the risk of infection at the point of pin penetration also is eliminated.

Another embodiment of the invention comprises an orthosis for immobilizing a region of a patient's body utilizing the anti-slip skin adhesion aspect of the present invention. In this embodiment of the invention, the orthosis comprises a rigid outer frame and a flexible orthotic support member secured to the outer frame for contacting a region of the body to be immobilized. The orthotic support member includes an adjustable fastening system for drawing the orthotic support member into pressure contact with the region of the body to be immobilized. A skin adhesion layer secured to the orthotic support member contacts the skin of the patient in the area immobilized by the orthosis. The skin adhesion layer comprises a non-skid surface for enhancing frictional contact with the skin to avoid slippage between the orthotic support member and the skin when the support member is held in immobilizing pressure contact with the bodily region. The invention may be used, for example, in a hip brace, an arm brace, a leg or knee brace, or a cervical-thoracic orthosis.

These and other aspects of the invention will be more fully understood by referring to the following detailed description and the accompanying drawings.

DETAILED DESCRIPTION

Figure 1:
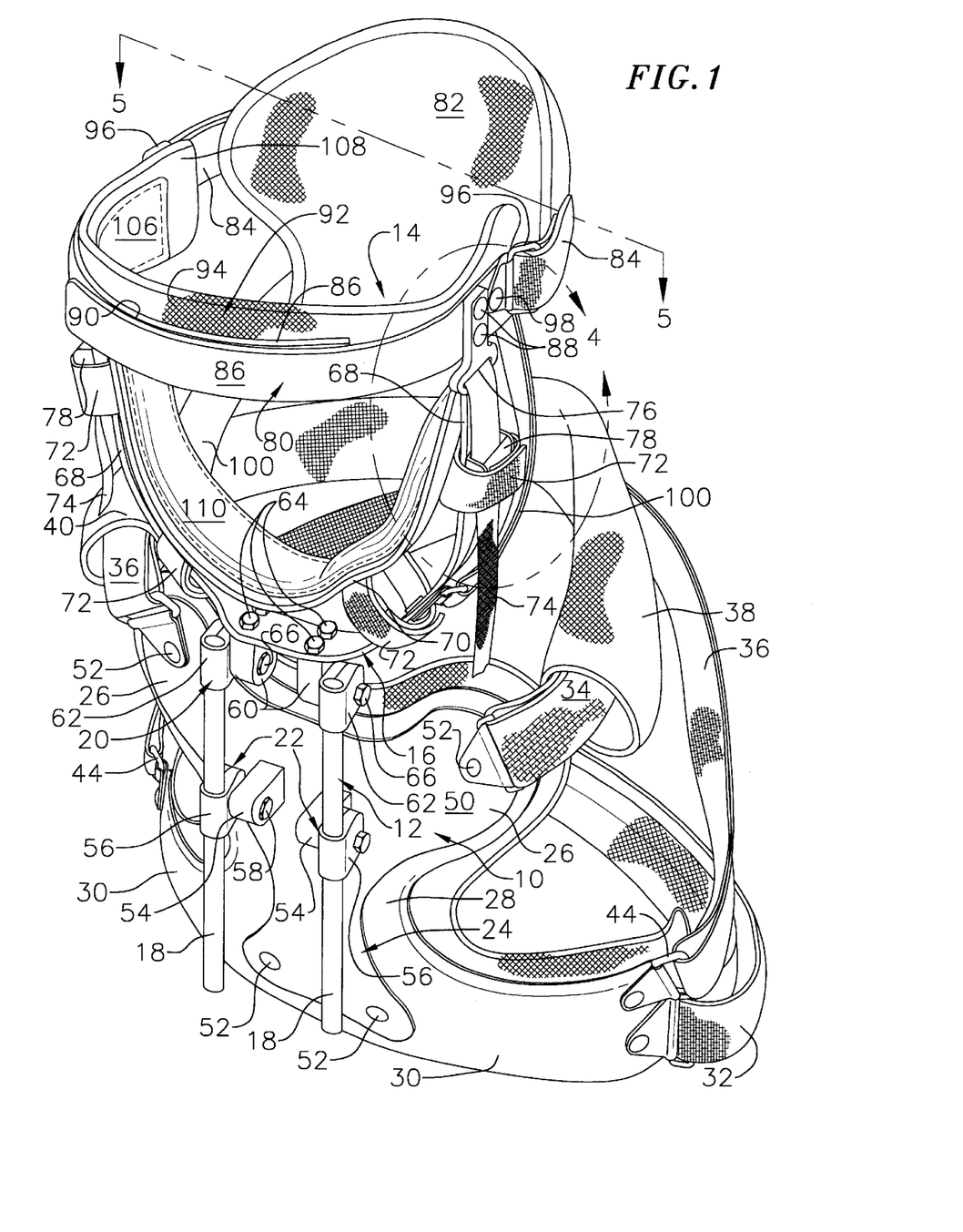
FIG. 1 is a perspective view of a preferred embodiment of a non-invasive halo-type cervical brace according to principles of this invention.

Referring to FIG. 1, a halo-type cervical brace comprises a reinforced anterior vest 10 which overlies the chest region of a patient. The anterior vest carries an upright rigid frame structure 12 which holds an immobilizing halo mask 14 secured around the head of the patient. The rigid frame structure includes a rigid U-shaped halo frame 16 which extends under the chin and around the sides of the patient's head. The upright frame structure also includes a pair of vertically extending and parallel rigid frame members 18 adjustably affixed to the bottom of the U-shaped halo frame via an upper pair of adjustable clamps 20. The upright frame structure further includes a lower pair of adjustable clamps 22 securing the parallel frame members to the front of the anterior vest. The adjustable lower clamps can be adjusted to allow rotation of the parallel frame members 18 relative to the anterior vest. The adjustable upper clamps 20 can be adjusted to allow rotation of the halo mask 14 relative the upper ends of the parallel frame members 18. These independent rotational adjustments allow the fixed orientation of the U-shaped halo frame 16 to be adjusted in rotation and in anterior-posterior position along the sides of the patient's head. The adjustable lower clamps 22 also provide a separate means of vertical adjustment of the parallel frame members 18 relative to the lower clamps for adjusting the elevation of the halo mask 14 above and with respect to the anterior vest 10.

The anterior vest preferably includes a semi-rigid breastplate 24 having outwardly and upwardly projecting upper regions 26 which overlie the upper outer portions of the patient's chest area, tapering downwardly toward a narrowed intermediate section 28 which then tapers outwardly to form a pair of elongated laterally extending protrusions 30 near the waist area of the patient. The breastplate is preferably made of a semi-rigid plastic material such as polypropylene. The lateral protrusions 30 extend around the front and sides of the patient's waist and fasten to flexible waist straps 32 which extend around and behind the patient's back. The waist straps can be adjustably loosened or tightened in the conventional manner with cooperating friction fasteners so that the waist portion of the anterior vest encircles the patient's torso and is adjustably secured in a fixed position around the patient's waist.

A pair of left and right flexible shoulder straps 34 and 36 are secured to the projecting upper regions 26 of the breastplate. The shoulder straps carry padded sleeves 38 and 40, respectively, extending along upper portions of the shoulder straps and over the shoulders of the patient. The remote ends of the shoulder straps 34 and 36 cross over behind the patient's back and fasten to the protruding left and right waist sections 30 of the breastplate in a manner similar to a harness.

Figure 7:
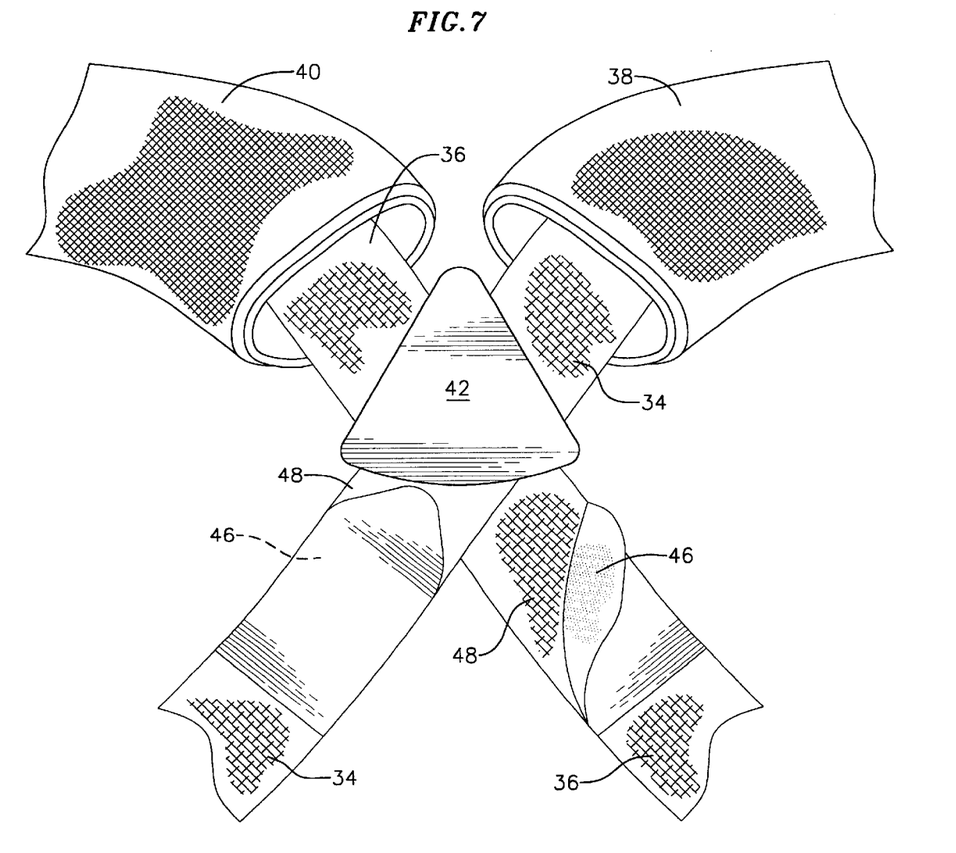
FIG. 7 is a fragmentary rear elevational view showing a means of adjusting a vest harness around the patient's back.

The rear elevational view of FIG. 7 best illustrates use of the harness for securing the anterior vest 10 to the patient. The rear portion of the harness includes a generally triangular-shaped sleeve 42 normally positioned at the rear center of the patient's back. The free ends of the shoulder straps 34 and 36 extend diagonally across the patient's back and are crossed over by threading them through the sleeve 42. The free ends of the shoulder straps then extend downwardly and forwardly to corresponding fastener rings 44 (see FIG. 1) on opposite ends of the waist portions 30 (see FIG. 1) of the breastplate. Here the free end portions of the shoulder straps are threaded through the fastener rings 44 and are then folded over and extended upwardly to overlie themselves so that friction fastener end portions 46 at the remote ends of the shoulder straps are secured by frictional contact to corresponding friction fastener surfaces 48 on the outside surface of each shoulder strap near the triangular sleeve. By crossing the shoulder straps behind the patient's back and drawing them through the fastener rings 44 on the lower corners of the breastplate and fastening them by the adjustable friction fasteners 46, the harness can be adjustably fastened to the patient's upper torso in a fixed position adjustable for each size patient.

Referring again to FIG. 1, the anterior vest also includes a reinforcing front plate 50 made of a semi-rigid reinforcing material such as nylon or metal. The front plate is generally Y-shaped and overlies the front surface of the breastplate 24, projecting upwardly toward the protruding upper regions 26 of the breastplate, together with a narrowed intermediate region and a lower region at the front of the waist section. The reinforcing plate is secured to the breastplate by suitable fasteners 52. The reinforcing front plate 50 and breastplate 24 provide a sturdy base for supporting the lower pair of frame clamps 22 which hold the vertically extending rigid frame members 18 for the halo mask 14. The lower clamps 22 each preferably include a respective clamp base 54 rigidly affixed to the anterior vest and cooperating sleeve-like rotational members 56 which carry the vertical frame members 18. The rotational sleeve portions of each clamp can be loosened to allow the vertical frame members to slide up and down for adjusting the elevation of the halo mask. The rotational sleeve portions 56 of the clamps also can be loosened to allow the frame members to rotate about a common axis toward or away from the patient for adjusting the proper position of the halo mask around the patient's head. Cooperating lateral fasteners 58 in the clamps are used to make the adjustments and define the axis of rotation.

The upper clamps 20 comprise a separate rigid clamp base 60 rotatably secured to a corresponding sleeve-like upper clamp member 62. The clamp base 60 of each upper clamp assembly is rigidly secured to the bottom of the U-shaped halo frame by a pair of corresponding fasteners 64. Separate lateral fasteners 66 extend through each upper clamp assembly for adjustably rotating the position of the U-shaped halo frame 16 relative to the upper ends of the parallel frame members 18. The halo frame 16 thus is able to rotate about a lateral axis through the fasteners for affixing the fore and aft rotational orientation of the U-shaped halo frame relative to the patient's head.

Figure 2:
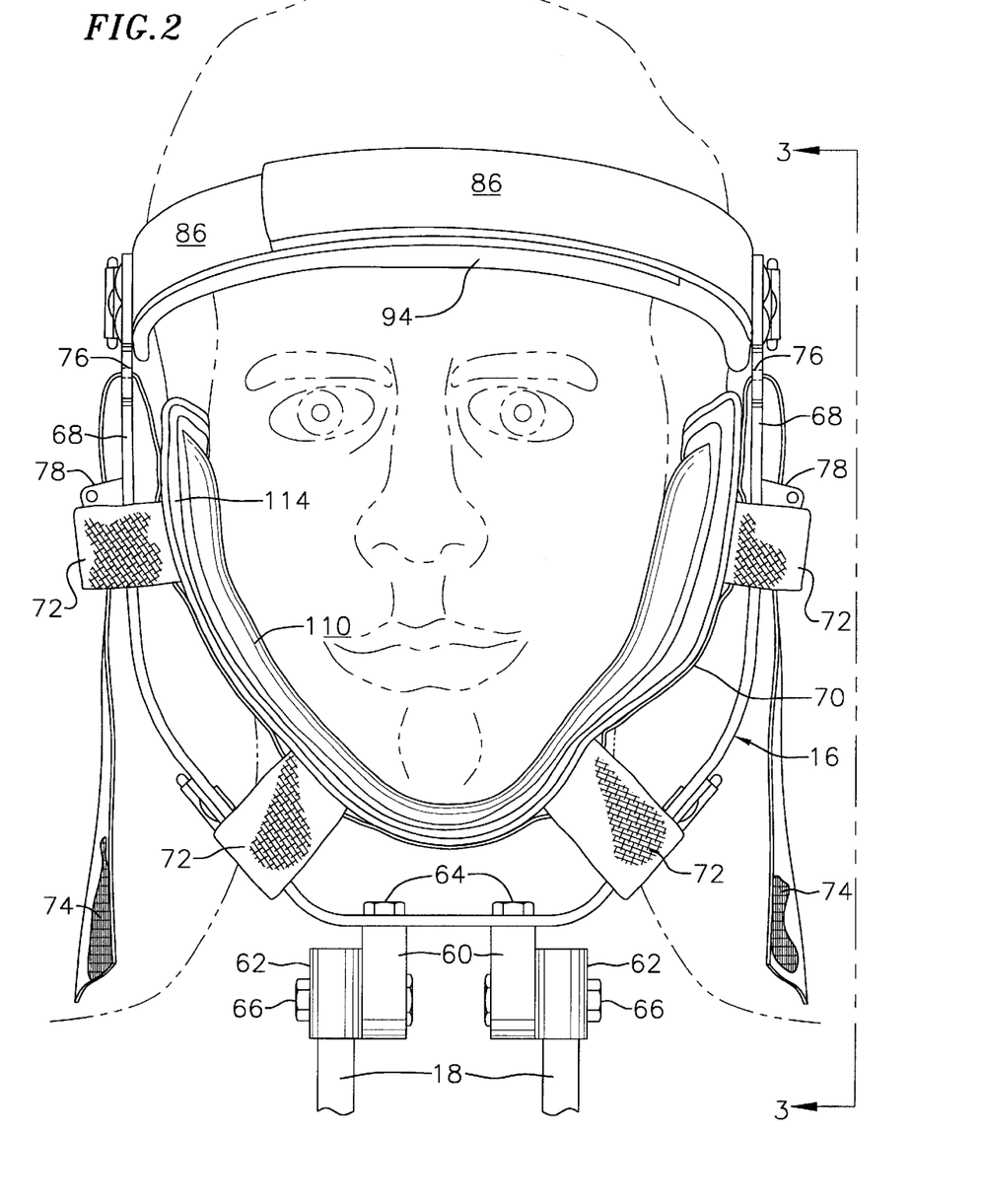
FIG. 2 is a fragmentary front elevational view showing a halo mask portion of the cervical brace in position around the head of a patient.

As mentioned previously, the halo mask 14 includes the upright rigid U-shaped halo frame 16 which extends under the patient's chin and around the sides of the patient's head. As shown in FIGS. 1 and 2, the upper ends 68 of the U-shaped halo frame 16 support the halo mask which includes a flexible generally U-shaped trapeze-type sling 70 carried within the U-shaped frame. The sling extends under the patient's chin and around the sides of the patient's head, generally in alignment with and spaced a short distance above the U-shaped halo frame. The U-shaped sling traverses the space between the uprights of the halo frame, is spaced above the bottom of the U-frame and is loosely attached along its length to the inside of the halo frame by spaced apart friction fasteners 72. The friction fasteners 72 are secured to the outside of the sling and looped around the rigid U-shaped halo frame. The free ends of the sling comprise flexible straps 74 which extend through corresponding slots 76 (shown best in FIGS. 3 and 4) on the upper ends 68 of the halo frame. The free ends of the straps then extend to the outside of the halo frame where respective clamp buckles 78 can be tightened to hold the sling in a fixed position within the halo frame. FIG. 4 shows the upper ends of the sling 70 passing through the slots 76 in the halo frame 16 and through the buckle clamps 78 shown in their open position. In this position the flexible free ends 74 of the sling 70 can be drawn through the slots in the rigid U-shaped halo frame 16 for pulling the sling tightly upwardly against the bottom of the patient's chin. When the proper alignment is set, the rotatable front portion of each clamp 78 can be rotated into its fixed clamped position (as shown in FIG. 1) for securing the free ends of the sling in the fixed set position. The base portion of each clamp 78 is rigidly affixed to the outside of the halo frame for maintaining the fixed set position of the sling.

The halo mask also includes a halo-type support which encircles the patient's head in a generally horizontal plane, extending around the forehead, along the sides of the patient's head generally above the ears, and around the back of the patient's head generally in the occipital region of the head. The halo-type support is a two-part structure comprising (1) a generally U-shaped semi-rigid forehead band 80 which extends around the forehead and along the sides of the patient's head, and (2) a padded occipital support 82 attached to the halo frame by flexible upper occipital straps 84 adjustable in length for securing, in part, the occipital support behind the patient's head.

The U-shaped forehead band 80 is adjustable in length and comprises a pair of opposed curved bars 86 affixed at their ends to the halo frame with their curved ends overlying one another adjacent the forehead of the patient. The forehead bars are rigidly affixed to the upper ends 68 of the rigid U-shaped halo frame by corresponding fasteners 88 and are also secured in their overlying relationship to one another by releasable friction fasteners 90 (see FIG. 5) on the confronting surfaces of the curved bars 86. In use, the forehead band components are semi-rigid, preferably made of a plastic material which can be conformed generally to the shape of the forehead. Their overlying relationship can be adjusted for also adjusting the effective length of the U-shaped forehead band 80 for holding it in a fixed position snugly along the forehead and around the sides of the patient's head.

Figure 5:
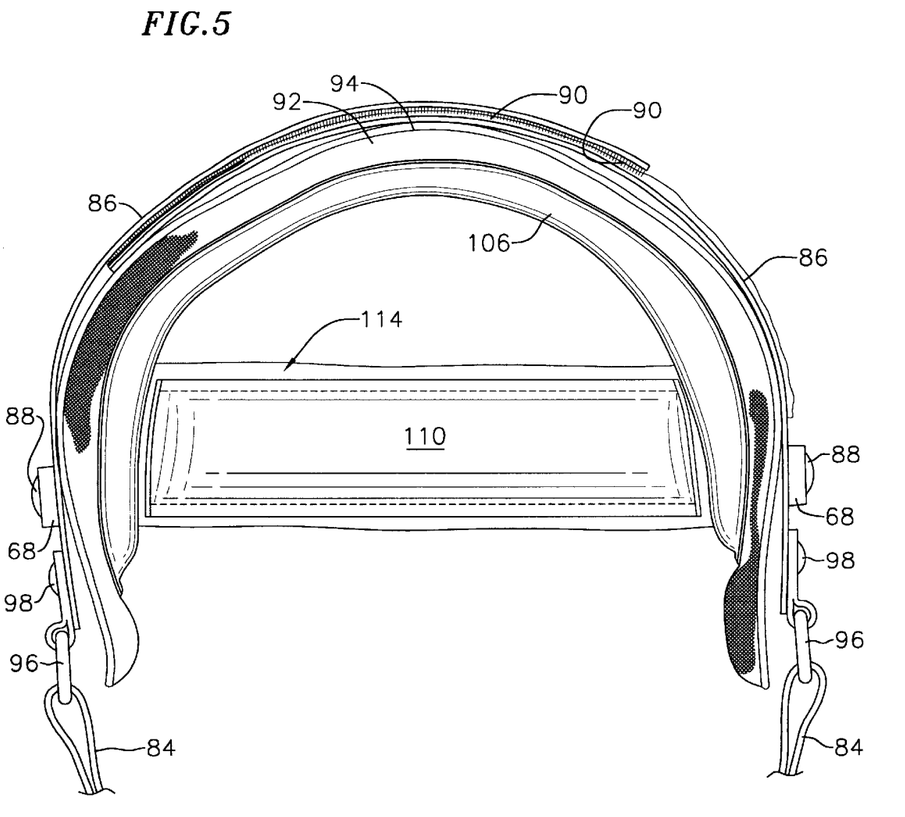
FIG. 5 is a top view showing skin adhesion layers attached to a chin support and to the inside of a forehead band.

Referring to FIG. 5, an elongated padded forehead strap 92 is releasably attached to the inside surface of the forehead band by cooperating friction fasteners 94. A friction fastener surface on the innermost forehead bar 86 releasably attaches to a cooperating friction fastener surface on the outside of the forehead strap 92.

The occipital support 82 is adjusted tightly against the back of the patient's head by its cooperating adjustable straps 84 to apply pressure in combination with the forehead band in a manner similar to a halo encircling the patient's head.

Figure 3:
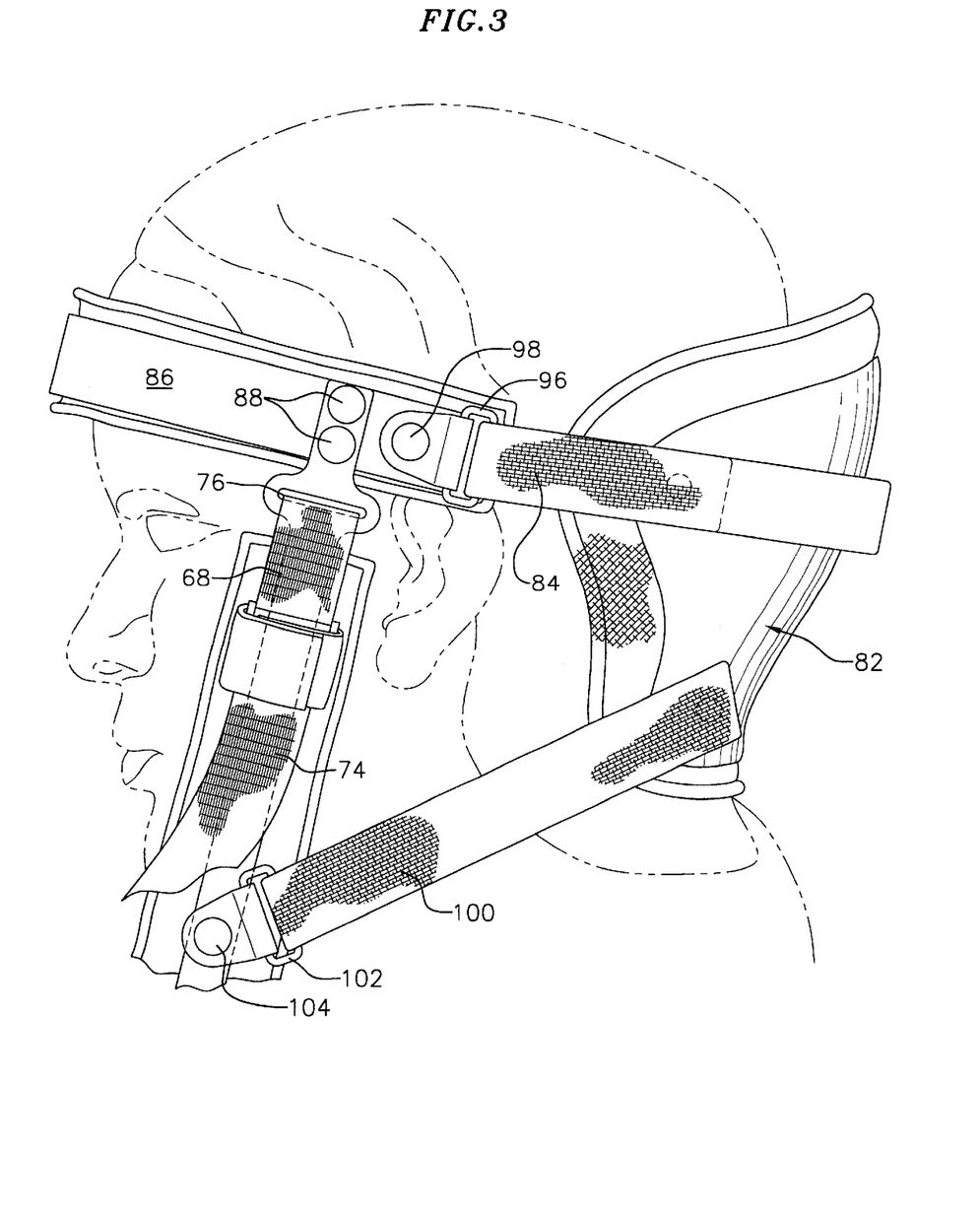
FIG. 3 is a side elevation view taken on line 3—3 of FIG. 2.
Figure 4:
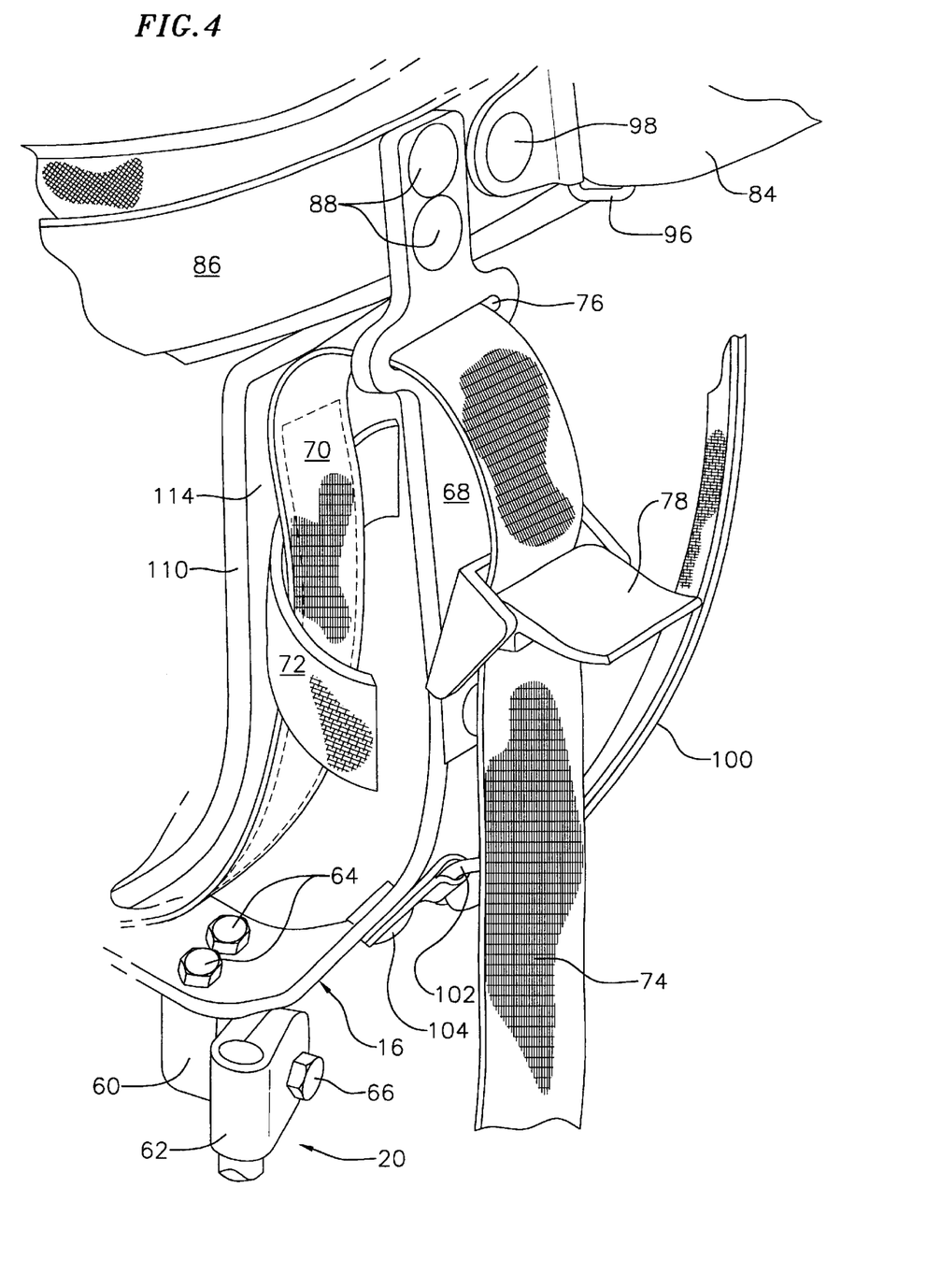
FIG. 4 is an enlarged perspective view taken within the circle 4 of FIG. 1 and showing various elements of a chin support adjustment system in an open unfastened position.

The side elevational view of FIG. 3 best illustrates adjustment of the occipital support 82. The upper front corners of the occipital support support the flexible upper straps 84 which extend through corresponding rotatable ring-type fasteners 96 affixed to the rear ends of the forehead bands by fasteners 98. Each fastener ring 96 is able to swivel about the axis of its corresponding fastener 98. The upper occipital straps 84 which are threaded through the ring fasteners 96 on the forehead bands are then folded back on themselves for overlaying them on the rear portions of the same straps. Cooperating layers of friction fastener material on the overlying portions of the straps 84 are frictionally attached to adjust the effective length of the straps. This securely holds the upper corners of the occipital support in place in contact with the back of the patient's head.

The lower corners of the occipital support 82 include diagonally extending fastener straps 100 which extend downwardly from the occipital support to corresponding lower ring fasteners 102 affixed to the outer surfaces of the U-shaped halo frame by fasteners 104. These lower diagonal occipital fastener straps 100 are similarly threaded through their corresponding ring fasteners 102 and folded back on themselves with corresponding friction fastener material providing a means of adjusting their effective length, and therefore the pressure, of the lower portion of the occipital support against the occipital region of the patient's head.

Elongated skin adhesion layers are affixed to the inside of the U-shaped forehead band 80 for applying pressure to the forehead and also to the inside of the sling 70 which extends under and applies pressure to the patient's chin. The skin adhesion layers include an upper skin adhesion layer 106 on the inside of the forehead band which is carried on the inside of the flexible forehead strap 92.

Figure 6:
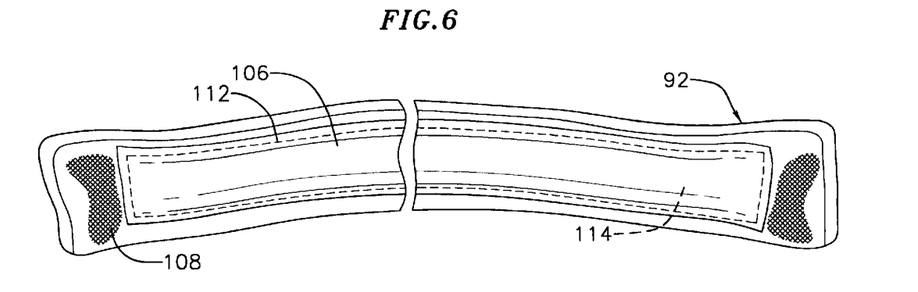
FIG. 6 is a perspective view showing a releasable forehead band with a skin adhesion layer.

As shown best in FIG. 6, the forehead strap 92 comprises a padded layer 108 of a friction fastener material for cooperating with a friction fastener material on the inside of the forehead band 14 for adjustably and releasably positioning the skin adhesion layer 106 on the inside of the forehead band. Separately, a skin adhesion layer 110 on the inside of the sling 70 is secured to the sling so as to face upwardly toward the underside of the patient's chin and along the sides of the patient's mandible. This holds the skin adhesion layer 110 tightly in pressure contact with the patient's skin in this region when the sling is adjusted to its fixed position.

Preferably the skin adhesion layers 106 and 110 comprise regions of a non-skid silicone gel material capable of frictionally adhering to the patient's skin for long periods of time without detrimental effects to the patient's skin or comfort during use. The skin adhesion layers in combination with the forehead band and the sling enhance immobilization of the halo mask by preventing relative motion between a patient's skin and the forehead strap and sling.

The skin adhesion layers 106 and 110 are preferably made from a reinforced layer of thermoplastic silicone gel or similar material having a somewhat tacky surface which provides frictional contact or traction with the skin when held in tight contact with the skin. The skin adhesion material is an inert material which can be worn against the skin for a long period of time without causing skin irritations or discomfort to the user. The presently preferred material is a silicone gel such as Walco Silicone V-1082 HiPro Clear which is available as a gel mixed with a promoter and poured onto a reinforcing layer. Preferably, the gel is poured onto a flexible layer of Tricot nylon or other similar flexible fabric material (such as a woven fibrous material) which can absorb the gel material and maintain it as a thin layer of uniform thickness on its surface. The preferred thickness of the gel layer in the finished part is about 1/16 inch and the Tricot nylon is about 0.003 inch in thickness. The gel layer is reinforced with the nylon or other similar reinforcing layer having a tensile strength which greatly exceeds that of the film of gel material which covers the surface of the underlying reinforcing layer. The reinforcing material avoids tearing and more easily fastens the gel material to the supporting Velcro fasteners.

FIG. 6 illustrates the releasable forehead strap 92 in which the reinforced gel layer 106 is affixed to the friction fastener surface by peripheral stitching 112. This view also illustrates the reinforcing layer 114 which securely holds the gel layer to the inside of the forehead strap. A similar means of reinforcing is used for the lower gel layer 110 secured to the inside of the sling. As shown best in FIG. 2, the lower gel layer 110, reinforced with the nylon layer, is secured to the inside of a padded layer 114 which in turn is carried on the inside of the sling 70.

In use, the halo is held around the patient's head by first adjusting the pressure of the halo around the head by appropriate adjustments to the forehead bars and the occipital support. This holds the skin adhesion layer 106 in non-slip contact with the patient's skin along the forehead and the sides of the head. Separately, the trapeze-type sling is adjusted in length to apply the proper pressure under the patient's chin and along the sides of the patient's head with the non-slip skin adhesion layer 110 in firm contact with the skin. The upper halo portion and the chin supporting portion of the halo mask cooperate to immobilize the patient's head in a non-invasive arrangement which avoids using skull pins for immobilization. Although the skin may have some slight motion relative to the halo, the present invention provides substantially complete immobilization sufficient to supplant use of the skull pin-type halo cervical braces for a high percentage of medical applications.

The present invention has been described with respect to an adult version of the cervical brace. An alternative form of the invention (not shown) has applications for pediatric use. The two spaced-apart frame members and their related clamps for setting orientation of the halo frame can be replaced with a single upright frame member secured to the U-shaped halo frame by a ball clamp. The ball clamp provides for rotational adjustments of the halo frame similar to that described above but can also be used to hold the halo frame in a tilted immobilizing position. This can be used, for example, in post operative treatment of Torti Collis by capturing the patient's head and preventing it from rotating while held in an angled position relative the body.

To summarize, the ultimate choice for the most effective cervical spine immobilization is the halo with skull pins. The cervical thoracic orthosis similar to that described in my U.S. Pat. No. 4,628,913 is the next most immobilizing orthosis currently available. There is a great immobilization differential between these two orthoses. The halo immobilizes the cervical spine about 96% while cervical thoracic orthosis of the '913 patent immobilizes the same area at about 70%. The non-invasive halo of this invention bridges the immobilization differential or gap between these two orthoses.

The treatment concept behind the present non-invasive halo design is the face mask with its open ring halo frame having the trapeze-like floating chin support and the horizontal forehead band opposed by the occipital support. The halo frame, trapeze and forehead band (which comprise the halo face mask) provide the immobilization lock which is similar to the traditional halo without the use of invasive pins. A key component to the immobilization lock is the skin adhesion system incorporated into the areas of skin contact.

The anterior halo vest that is fastened to the anterior thoracolumbar region is easy to apply without the need for side to side turning or "log-rolling." Because there is no posterior vest, posterior skin breakdown or ulcerations caused by vest pressure are non-existent. The halo vest and face mask are connected by the double upright system with the halo clamps. Flexion-extension, anteroposterior translation and distraction adjustments are possible.

The halo vest and halo face mask are fitted and adjusted separately. Halo mask mediolateral (M-L) changes can be widened or narrowed by hand or with bending irons. The forehead band can be raised or lowered while it is on the patient's head. The occipital piece is connected by the four separate Velcro straps to the halo mask for further adjustments. Finally, the halo vest and mask are connected in the relative desired alignment by the upper and lower sets of clamps.

The silicone gel skin contact prevents the chin from sliding forward. In the event that the chin slides forward, an anterior chin strap can be added to provide further control.

Although the invention has been described with reference to the cervical orthosis, the immobilizing skin adhesion aspect of the invention also can be used with other orthotic devices. For instance, the skin adhesion layer may be incorporated into a hip brace, an arm brace, a leg or knee brace, or a cervical-thoracic orthosis such as that described in my U.S. Pat. No. 4,628,913. In each such brace, the orthosis comprises a rigid outer frame and a flexible orthotic support member secured to the outer frame for contacting the region of the body to be immobilized. The orthotic support member includes an adjustable fastening system for drawing the orthotic support member into pressure contact with the immobilized region of the body. A skin adhesion layer secured to the orthotic support contacts the skin of the patient in the area being immobilized. The skin adhesion layer comprises a non-skid surface for enhancing frictional contact with the skin to avoid slippage between the orthotic support member and the skin when the support member is held in immobilizing pressure contact with the bodily region. As with the cervical orthosis, the skin adhesion layer preferably comprises a layer of a non-skid plastic material adhered to a flexible reinforcing sheet having a substantially greater tensile strength than the skin adhesion layer. The skin adhesion layer forms a thin surface film along the length of the reinforcing layer. In one embodiment the skin adhesion layer comprises a silicone gel layer impregnated in and forming the non-skid surface on the reinforcing sheet which, as mentioned previously, can comprise a woven fibrous layer such as woven nylon.

I claim:

1. A non-invasive cervical brace, comprising:
   a vest for fastening in a fixed position around the chest area of a patient,
   a halo mask positionable around the patient's head, the halo mask conformable to encircle the patient's head extending around and in pressure contact with the forehead, along opposite sides and around the back region of the patient's head,
   a rigid brace structure secured to the vest at a central front portion and adapted to extend upwardly to the vicinity of the patient's head for attachment to the halo mask to hold the halo mask in a fixed position around the patient's head for immobilizing the head of the patient, and
   a skin adhesion layer extending along at least an inside surface of a region of the halo mask overlying and in pressure contact with the forehead of the patient during use, the skin adhesion layer comprising a material which enhances frictional contact between the pressure-applying forehead region of the halo mask and the skin of the patient to avoid slippage between the skin and the halo mask to thereby improve the immobilizing effect of the halo mask on the patient's head,
   in which the rigid brace structure includes an upright generally U-shaped rigid halo frame for extending under the patient's chin and upwardly along opposite sides of the patient's head during use, the halo mask rigidly affixed to upper end portions of the U-shaped halo frame.

2. The brace according to claim 1 in which the halo mask further includes a chin support adjustably positionable in pressure contact with the chin region of the patient and adapted to extend upwardly along the sides of the patient's head, the chin support attached to the rigid brace structure for maintaining the chin support in fixed pressure contact with the chin region of the patient, and further including a skin adhesion layer for extending along an inside surface of the chin support for pressure contact with the chin region of the patient and comprising a material which enhances frictional contact between the chin support and the skin of the patient to prevent slippage and thereby further improve the immobilizing effect of the halo mask on the patient's head.

3. The brace according to claim 1 in which the halo mask includes a curved forehead band for extending along the patient's forehead and along opposite sides of the patient's head for attachment to the upper end portions of the U-shaped halo frame for providing a front portion of a halo ring extending around the patient's head.

4. The brace according to claim 3 in which the forehead band comprises a pair of curved bars overlying one another with releasable fasteners for securing them together in an adjusted length, and in which ends of the curved bars are rigidly affixed to the upper end portions of the U-shaped halo frame.

5. The brace according to claim 3 in which the halo mask further includes a chin support adjustably positionable in pressure contact with the chin region of the patient and adapted for extending upwardly along the sides of the patient's head, the chin support attached to the upper end portions of the rigid U-shaped halo frame for maintaining the chin support in fixed pressure contact with the chin region of the patient, and further including a skin adhesion layer extending along an inside surface of the chin support for pressure contact with the chin region of the patient and comprising a material which enhances frictional contact between the chin support and the skin of the patient to prevent slippage and thereby further improve the immobilizing effect of the halo mask on the patient's head.

6. The brace according to claim 5 in which the halo mask further includes an occipital support adjustably fastened to the forehead band of the halo mask for extending in a posterior direction away from the forehead band and adjustable to apply pressure to the occipital region of the patient's head for providing a rear portion of a halo ring extending around the patient's head.

7. The brace according to claim 3 in which the halo mask further includes an occipital support adjustably fastened to the forehead band of the halo mask for extending in a posterior direction away from the forehead band and adjustable to apply pressure to the occipital region of the patient's head for providing a rear portion of a halo ring extending around the patient's head.

8. The brace according to claim 1 in which the rigid brace structure includes a ball clamp for adjustably securing the halo mask in a tilted position for use of the halo mask in pediatric treatment.

9. The brace according to claim 1 in which the skin adhesion layer comprises a layer of a non-skid plastic material adhered to a flexible reinforcing sheet having a substantially greater tensile strength than the skin adhesion layer, the skin adhesion layer forming a thin surface film along the length of the reinforcing layer.

10. The brace according to claim 9 in which the skin adhesion layer comprises a silicone gel layer impregnated in and forming said non-skid surface on the reinforcing sheet.

11. The brace according to claim 10 in which the reinforcing sheet comprises a woven fibrous layer.

12. The brace according to claim 1 in which a chin support is positioned inside the U-shaped halo frame and adapted for pressure contact with the chin region of the patient.

13. A non-invasive cervical brace, comprising:
a vest for fastening in a fixed position around the chest area of a patient,
a halo mask positionable around the patient's head, the halo mask conformable to encircle the patient's head extending around and in pressure contact with the forehead, along opposite sides and around the back region of the patient's head,
a rigid brace structure secured to the vest and adapted to extend upwardly to the vicinity of the patient's head for attachment to the halo mask to hold the halo mask in a fixed adjustable position around the patient's head for immobilizing the head of the patient,
the rigid brace structure including an upright generally U-shaped rigid halo frame for extending under the patient's chin and upwardly along opposite sides of the patient's head during use,
the halo mask including a curved forehead band for extending along the patient's forehead and along opposite sides of the patient's head for attachment to upper end portions of the U-shaped halo frame for providing a front portion of a halo ring encircling the patient's head,
the halo mask further including an occipital support adjustably fastened to the forehead band of the U-shaped halo frame for extending in a posterior direction away from the forehead band and adjusted to apply pressure to the occipital region of the patient's head, the occipital support providing a rear portion of the halo ring encircling the patient's head during use, and
a skin adhesion layer extending along at least an inside surface of a region of the forehead band overlying and in pressure contact, with the forehead of the patient during use, the skin adhesion layer comprising a material which enhances frictional contact between the pressure applying forehead region of the halo mask and the skin of the patient to avoid slippage between the skin and the halo mask to thereby improve the immobilizing effect of the halo mask on the patient's head.

14. Apparatus according to claim 13 in which the halo mask further includes a chin support adjustably positionable in pressure contact with the chin region of the patient and extending upwardly along the sides of the patient's head, the chin support attached to the rigid halo frame for maintaining the chin support in fixed pressure contact with the chin region of the patient, and further including a skin adhesion layer extending along an inside surface of the chin support for pressure contact with the chin region of the patient and comprising a material which enhances frictional contact between the chin support and the skin of the patient to prevent slippage and thereby further improve the immobilizing effect of the halo mask on the patient's head.

15. Apparatus according to claim 13 in which the forehead band comprises a pair of curved bars overlying one another with releasable fasteners for securing them together in an adjusted length, and in which ends of the curved bars are rigidly affixed to the upper end portions of the U-shaped halo frame.

16. Apparatus according to claim 13 in which the skin adhesion layer on the forehead band is releasably attachable to the forehead band.

17. Apparatus according to claim 15 in which the skin adhesion layer on the forehead band is releasably attachable to the forehead band.

18. Apparatus according to claim 17 in which the skin adhesion layer comprises a silicone gel layer impregnated in and forming said non-skid surface on the reinforcing sheet.

19. The brace according to claim 13 in which a chin support is positioned inside the U-shaped halo frame and adapted for pressure contact with the chin region of the patient.

20. A non-invasive cervical brace, comprising:
a vest for fastening in a fixed position around the chest area of a patient,
a halo mask positionable around the patient's head, the halo mask conformable to encircle the patient's head extending around and in pressure contact with the forehead, along opposite sides and around the back region of the patient's head,
a rigid brace structure secured to the vest and adapted to extend upwardly to the vicinity of the patient's head for attachment to the halo mask to hold the halo mask in a fixed position around the patient's head for immobilizing the head of the patient, and
a skin adhesion layer extending along at least an inside surface of a region of the halo mask overlying and in pressure contact with the forehead of the patient during use, the skin adhesion layer comprising a material which enhances frictional contact between the pressure-applying forehead region of the halo mask and the skin of the patient to avoid slippage between the skin and the halo mask to thereby improve the immobilizing effect of the halo mask on the patient's head,
in which the rigid brace structure includes an upright generally U-shaped rigid halo frame for extending under the patient's chin and upwardly along opposite sides of the patient's head during use, the halo mask rigidly affixed to upper end portions of the U-shaped halo frame, and
in which a chin support is positioned inside the U-shaped halo frame and adapted for pressure contact with the chin region of the patient.

21. A non-invasive cervical brace, comprising:
a vest for fastening in a fixed position around the chest area of a patient,
a halo mask positionable around the patient's head, the halo mask conformable to encircle the patient's head extending around and in pressure contact with the forehead, along opposite sides and around the back region of the patient's head,
a rigid brace structure secured to the vest and adapted to extend upwardly to the vicinity of the patient's head for attachment to the halo mask to hold the halo mask in a fixed adjustable position around the patients head for immobilizing the head of the patient,
the rigid brace structure including an upright generally U-shaped rigid halo frame for extending under the patient's chin and upwardly along opposite sides of the patient's head during use, in which a chin support is positioned inside the U-shaped halo frame and adapted for pressure contact with the chin region of the patient, the halo mask including a curved forehead band for extending along the patient's forehead and along opposite sides of the patient's head for attachment to upper end portions of the U-shaped halo frame for providing a front portion of a halo ring encircling the patient's head during use, the halo mask further including an occipital support adjustably fastened to the forehead band of the halo mask for extending in a posterior direction away from the forehead band and adjusted to apply pressure to the occipital region of the patient's head, the occipital support providing a rear portion of the halo ring encircling the patient's head, and a skin adhesion layer extending along at least an inside surface of a region of the forehead band overlying and in pressure contact with the forehead of the patient during use, the skin adhesion layer comprising a material which enhances frictional contact between the pressure applying forehead region of the halo mask and the skin of the patient to avoid slippage between the skin and the halo mask to thereby improve the immobilizing effect of the halo mask on the patient's head.

* * * * *